US00PP12425P2

(12) United States Plant Patent
Kulkarni et al.

(10) Patent No.: US PP12,425 P2
(45) Date of Patent: Feb. 26, 2002

(54) *PELARGONIUM GRAVEOLENS* PLANT NAMED 'NARMADA'

(75) Inventors: Raghavendra Narayanrao Kulkarni; Nagawara Seshagirirao Ravindra; Srinivas Iyer Ramesh; Gopal Rao Mallavarapu; Suman Preet Singh Khanuja; Mahendra Pandurang Darokar; Ajit Kumar Shasany; Sushil Kumar, all of Lucknow (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 09/537,173

(22) Filed: Mar. 29, 2000

(51) Int. Cl.[7] ..... A01H 5/00
(52) U.S. Cl. ..... Plt./258
(58) Field of Search ..... Plt./258

(56) References Cited

PUBLICATIONS

P.N. Kaul, et al., "Volatile Constitutents of Three Cultivars of Rose–Scented Geranium (Pelargonium Sp.) as Influenced by Method of Distillation," Pafai Journal, Oct.–Dec. 1995, pp. 21–26.

Sri A. Y. Swamy, et al. "Cultivation of Scented Geranium (*Pelargonium Graveolens*) on the Nilgiris," Indian Perfumer, vol. IV, Part I, 1960, pp. 3–9.

A. M. Humphrey, et al. "Application of Gas–Liquid Chromatography to the Analysis of Essential Oils Part XV. * Determination of 'Rhodinol' in Oils of Geranium," Analyst, vol. 115, Apr., 1990, pp. 459–462.

B.V. Charlwood, "XX Pelargonium spp. (Geraniumo): In Vitro Culture and the Production of Aromatic Compounds," Biotechnology in Agriculture and Forestry, vol. 15, Medicinal and Aromatic Plants III (ed. By Y.P.S. Bajaj), 1991, pp. 339–352.

B.R. Rajeswara, et al., "History and botanical nomenclature of rose scented geranium culitvars grown in India," Indian Perfumer, 36 (2), 1992, pp. 155–161.

Gopal R. Mallavarapu, et al., "Chemical and Agronomical Investigations of a New Chemotype of Geranium," J. Essent. Oil Res., 5, Jul./Aug. 1993, pp. 433–438.

P. Teisseire, "7 Industrial Quality Control of Essential Oils by Cappillary GC," pp. 237–247.

*Primary Examiner*—Bruce R. Campell
*Assistant Examiner*—A Para
(74) *Attorney, Agent, or Firm*—Smith, Gambrell & Russell, LLP

(57) ABSTRACT

The invention is related to the development of a new and distinct geranium plant called e 'Narmada' yeilding perfumery oil having higher content of rhodinol, total alcohol and high citronellol/geraniol ratio and lower content of undesirable isomenthone and 10-epi-γ-eudesmol.

2 Drawing Sheets

FIELD OF INVENTION

The invention is related to the development of a novel geranium plant 'Narmada' derived as a somaclonal variant "CIMAP/GER SA 44" from the Indian cultivar 'Bourbon'. The invention is related to the development of a plant which possesses desirable high percentage of cis- and trans- rose oxides, free rhodinol (linalool+citronellol+geraniol) and total rhodinol (linalool+citronellol+geraniol+citronellyl formate+geranyl formate) which contribute to perfumery value of essential oil of geranium. The somaclone "CIMAP/GER SA EE" now named 'Narmada' is propagated vegetatively through stem cuttings and is stable for commercial cultivation.

BACKGROUND OF THE INVENTION

*Pelargonium graveolens* L Herit commonly known as 'rose scented geranium' yields an essential oil on distillation of its above ground fresh biomass which is common known as 'Oil of Geranium'. It is a native to the dry slopes of Cape Province of South Africa and has spread to different parts of the world. In India, it was introduced in the early part of the present century. The highest quality oil possesses a delicate rose-line fragrance and is used in perfumes and flavors, while the lower quality oil has been widely used in general purpose perfumes for hand creams, soaps and other toilet requisites.

Commercial geranium oil is a mixture of 120 mono and sesquiterpenes and low molecular weight aroma compounds. The main constituents are citronellol, geraniol, linalool and formates of geraniol and citronellol which constitute about 60–70% of total oil.

Three types of geranium oil are recognised in trade viz, Reunion or Bourbon, African or Egyptian and Chinese. The Chinese geranium oil is characterized by its larger citronellol; geraniol ratio of 3–4:1 as compared with the ratio 1:1 in Bourbon and Egyptian geranium oils. 'Bourbon' and 'Egyptian' geranium oils are distinguished by their relative contents of guaia-6,9-diene and 10-epi-γ-eudesmol.

In India, only two varieties are grown. (1) 'Bourbon' or 'Reunion' and (2) 'Algerian' or 'Tunisian'. The essential oil of the Indian cultivar 'Bourbon' resembles the African geranium oil. The essential oil of the cultivar 'Algerian' resembles the Chinese geranium oil in its ratio of citronellol:geraniol. Recently, introduction of another clone has been reported but its oil has a citronellol:geraniol ratio 1:5. So, for the farmers cultivating geranium and the industries, the choice of oil is limited due to limited cultivars, the yield of which have remained constant since long.

Further, geranium is propagated vegetatively by stem cuttings as these plans do not flower or flower sparsely and, generally, do not produce any seeds in India. Genetic improvement by sexual methods of breeding is extremely difficult. As these cultivars have been propagated only vegetatively over a long period of time, somaclonal variation through tissue culture can be expected to be a desirable approach in genetic improvement through selection. Keeping these factors in mind this new improved clone of the invention, CIMAP/GER-SA 44 of *Pelargonium graveolens* was derived as a somaclonal variant from the Indian cultivar, 'Bourbon' and named as 'Narmada'. The plants as asexually produced through cuttings remain true to type.

OBJECTS OF THE INVENTION

Accordingly, the main object of the invention is to develop a novel geranium plant 'Narmada'.

Another object is to develop a geranium plant that possesses high percentage of rose oxides, free rhodinol, total alcohol and high citronellol; geraniol ratio which contributes to the perfumery value of the essential oil yielded by the plant.

Yet another object is to develop novel geranium plant 'Narmada' yielding high percentage of essential perfumery oil and low content of undesirable "isomenthone and 10-epi-γ-erudesmol".

SUMMARY OF THE INVENTION

In accordance with above and other objects, the invention provides a novel plant 'Narmada' derived as a somaclonal variant CIMAP/GER SA 44 from the Indian cultivar, 'Bourbon' clone. Novel plant 'Narmada' has high percentage of cis- and trans- rose oxides, free rhodinol (linalool+citronellol+geraniol) and total rhodinol (linalool+citronellol+geraniol+citronellyl formate+geranyl formate) which contributes to perfumery value of essential oil of geranium. To the best of the Inventors' knowledge None of the parental cultivars are patented in the United States of America or the subject of a pending U.S. Application.

DETAILED DESCRIPTION OF THE INVENTION

Accordingly, the invention provides a new plant 'Narmada' of *Pelargonium graveolens* yielding high perfume value essential oil developed through tissue culture, possessing the following combination of characteristics:

a. Lettuce greenish leaves (137B), alternate, stipulate, simple with about 5 palmatisect primary lobes and pinnatisect secondary lobes, pubescent on both sides, b. Produces high yield of herbage to the extend of 380 to 490 gram per plant and yields oil to the extent of 0.25 to 0.30%, c. The plant has a high Citronellol/geraniol ratio 1.34±0.05 (0.59–2.48), producing significantly high free Rhodinol 64.21±0.33 (58.0–69.2) and total Rhodinol 76.98±0.4 (69.8–82.2) compared to the parent variety 'Bourbon', d. The essential oil of the plant is characterized by low content of isomenthone (0.05–2.0) and 10-epi-γ-eudesmol (0.4–4.0%) at different stages of growth, and e. The plant has distinct molecular profile by random amplified polymorphic DNA (RAPD) using 20 MAP primers distinguishing the plant from the other existing varieties.

The colour codes employed in the specification are according to R.H.S. Colour Chart published by The Royal Horticultural Society, 80 Vincent Square, London SWIP 2PE, 1995.

In the Accompanying drawings

FIG. 1. is a photograph that represents a typical geranium plant 'Narmada' of the invention.

FIG. 2 depicts the RAPD profile of the plant of the invention with MAP primers.

A new clone of *Pelargonium graveolens* was desired to be developed with higher percentage of cis- and trans- rose oxides, free rhodinol (linalool+citronellol+geraniol) and total rhodinol (linalool+citronellol+geraniol+citronellyl formate+geranyl formate) which are known to contribute to the perfumery value of essential oil of geranium.

Internodal explants of the Indian cultivar Bourbon were soaked in 0.1% aqueous solution of the mutagenic agent sodium azide for 5 hr. and incubated on Murashige and Skoog medium modified with 1.0 mg/1 of each benzyl amino purine and indole-3 acetic acid at 25±1° C. with 16 hr. light/8 hr. darkness. Upon induction and regeneration, the shoots were separated and rooted in half strength Murashige and Skoog medium with 0.5 mg/1 of indole-3 butyric acid. The young plantlets were hardened and planted in filed. About 200 of plants produced were evaluated for essential oil content and composition. One clone with lower contents of isomenthone and 10-epi-γ-eudesmol and higher contents of free rhodinol (linalool+citronellol+geraniol) and total rhodinol (linalool, citronellol, geraniol, citronellyl formate and geranyl formate) in its essential oil than the parental cultivar was identified. It was tested in V2 (vegetative 2) and V3 (vegetative 3) generation along with the parental Indian cultivar, 'Bourbon'. It was found to breed true for significantly higher content of both free rhodinol and total rhodinol than the parental cultivar. It also showed significantly lower contents of isomenthone and 10-epi-γ-eudesmol than the parental cultivar.

Stem cuttings of the 'Narmada' plant of the instant invention were planted in beds of 1.76 $m^2$ size (4 replications) arranged randomly in a field at the experimental farm of the Institute located at Bangalore, in the state of Karnataka (13.50N, 77.55E, 930 meters above sea level) during December 1997. The field blocks used were given a uniform dose of 100 kg/ha $P_2O_5$ and 60 kg/ha $K_2O$. Nitrogen was applied in three splits while phosphorous and potassium were applied at the time of planting. A light irrigation was given just after planting of stem cuttings and plots were manually weeded and irrigated at regular intervals of two weeks throughout the cropping season. The crops were allowed to grow until April when observations on the morphology of the plants were recorded and the crop was harvested to estimate the yield of herbage as well as yield and quality of essential oil. All experiments were conducted at the field station at Pantnagar, near Luncknow in Uttar Pradesh in India. The plant is asexually reproduced through stem cutting and true to type.

Evidence of uniformity and stability of plant Narmada

The new clone, CIMAP/GER SA 44 developed as the plant 'Narmada' has significantly higher content of free rhodinol (linalool+citronellol+geraniol) and total rhodinol (linalool, citronellol, geraniol, citronellyl formate and geranyl formate) and low contents of isomenthone and 10-epi-γ-eudesmol than parental cultivar. It also showed significantly higher citronellol/geraniol ratio than parental cultivar. These relative differences between the clone and the parental cultivar were consistent over different seasons and vegetative generations.

Statement of distinction

The new plant 'Narmada' possesses lettuce green leaves which are as pubescent like Indian cultivar of 'Bourbon' but less pubescent than the other Indian cultivar 'Algerian'. Its essential oil has significantly low contents of isomenthone and 10-epi-γ-eudesmol, higher citronellol/geraniol ratio and higher contents of free rhodinol and total rhodinol as compared with parental Indian cultivar of 'Bourbon' in vegetative-1, vegetative-2 generations (Table 1) four months after planting and in vegetative-3 generation (Table 2) 12 months after planting.

TABLE 1

Essential oil composition of plant 'Narmada' and parental cultivar in vegetative-1 and vegetative-2 generations after four months of planting

| | Vegetative-1 generation | | Vegetative-2 generation | |
|---|---|---|---|---|
| Oil constituents | Clone SA 44 'Narmada' | Parental cultivar | Clone SA 44 'Narmada' | Parental cultivar |
| Linalool | 11.8 | 5.5 | 6.5 | 8.0 |
| cis-Rose oxide | 0.7 | 0.1 | 1.1 | 0.2 |
| trans-Rose oxide | 0.3 | 0.07 | 0.4 | 0.2 |
| Menthone | 0.04 | 0.07 | 0.2 | 0.3 |
| Isomenthone | 1.4 | 4.2 | 1.8 | 8.3 |
| Citronellol | 36.8 | 17.5 | 26.7 | 15.4 |
| Geraniol | 21.2 | 37.4 | 26.9 | 32.8 |
| Citronellyl formate | 6.8 | 6.4 | 7.0 | 4.9 |
| Gernayl formate | 2.7 | 6.1 | 3.9 | 3.0 |
| 10-epi-γ-eudesmol | 1.3 | 6.5 | 2.0 | 5.9 |
| Citronellol/geraniol ratio | 1.74 | 0.47 | 0.99 | 0.47 |
| Free Rhodinol | 69.8 | 60.4 | 60.1 | 56.2 |
| Total Rhodinol | 79.3 | 72.9 | 71.0 | 64.1 |

TABLE 2

Mean and range of essential oil constituents of the plant 'Narmada' and parental cultivar over 12 months in vegetative-3 generation

| | Clone:CIMAP/GER | | Parental | |
|---|---|---|---|---|
| Oil constituents | SA 44 Mean SE* | Range | cultivar Mean SE* | Range |
| Linalool | 4.41 ± 0.13 | 2.3–7.9 | 4.37 ± 0.10 | 2.0–5.9 |
| Cis-Rose oxide | 0.34 ± 0.0014 | 0.1–0.5 | 0.34 ± 0.016 | 0.2–0.8 |
| Trans-Rose oxide | 0.15 ± 0.006 | 0.03–0.2 | 0.14 ± 0.009 | 0.08–0.4 |
| Menthone | 0.17 ± 0.009 | 0.04–0.3 | 0.18 ± 0.006 | 0.1–0.3 |
| Isomenthone | 0.60 ± 0.06 | 0.05–2.0 | 6.75 ± 0.10 | 5.2–8.7 |
| Citronellol | 33.05 ± 0.67 | 2.0 – 44.1 | 22.78 ± 0.29 | 17.5–26.0 |
| Geraniol | 26.75 ± 0.51 | 20.3–37.6 | 30.04 ± 0.45 | 24.0–36.6 |
| Citronellyl formate | 8.65 ± 0.14 | 6.4–11.0 | 6.89 ± 0.11 | 5.1–8.9 |
| Geranyl formate | 4.13 ± 0.10 | 2.6–6.2 | 5.1 ± 0.092 | 3.0–6.3 |
| 10-epi-γ-eudesmol | 1.54 ± 0.10 | 0.4–4.0 | 6.82 ± 0.11 | 5.6–10.2 |
| Citronellol/geraniol ratio | 1.34 ± 0.05 | 0.59–2.48 | 0.79 ± 0.02 | 0.51–1.1 |
| Free Rhodinol | 64.21 ± 0.33 | 58.0–69.2 | 57.19 ± 0.30 | 51.5–63.4 |
| Total Rhodinol | 76.98 ± 0.4 | 69.8–82.2 | 69.18 ± 0.26 | 65.4–74.7 |

*SE = Standard error

Randomly Amplified Polymorphic DNA analysis

The RAPD patterns of the plant are entirely distinguishable from those of the parents as well as of other geranium varieties as analyzed with the MAP primers. The following primers were used to develop a unique and distinct RAPD profile (FIG. 2) of the plant of this invention. From the analysis, a difference of about 26% was calculated out for the plant of invention with the parent variety 'Bourbon'.

Description of the new Plant 'Narmada' of *Pelargonium graveolens*. The plant 'Narmada' is bushy and has a shape of a canopy. The flowers are produced in axillary racemes. Flowers appear in the months of April through May. The pedicel is green with bracts, calyx: green, pubescent with 5 sepals. Corolla: Purple (78C) with violet dark streaks on the upper lip; 5 sepals in all. The androcium has 5 stamens, fused at the base. The gynoecium has 5 carpels. The stigma is filamentous and branched. No seed formation is observed.

Genus: Pelargonium.
Species: Graveolens L.
Family: Geraniaceae.
Common name: Geranium.
Growth habit: Erect, uniform.
Stem cylindrical, woody at base, pubescent, green when young, turning brown with age. Other botanical characteristics include:

*Habit.*—Erect, uniform.
*Canopy.*—Spread is about 60 cm diameter and 50 cm height.
*Stem.*—Moderately hairy, sturdy, woody at base usually 7–8 primary branches, cylindrical, woody; pubescent green (191C) when young turns brown (199D) with age.
*Leaf petiole.*—Medium size, thin, rough dark pink at base.
*Leaf lamina.*—Very large (6 cm long and 8 cm wide), Lamina has 76 lobes, lettuce green 173B on the upper surface and 147D color on the lower surface. Leaves are alternate and stipulate.
*Leaf trichomes.*—Medium (500 μm), thin.
*Flower.*—Medium size (<1.5 cm), dark pink petals 78C with violet streaks on the upper lip of the flower, yellow fertile anthers.
*Essential oil content.*—0.25–0.30%.
*Physical appearance of oil.*—Bright yellow.
*Seed formation: None.*

All color numbers are as per the International Royal Horticultural Society Index.

Leaf Lettuce green (137B), alternate, stipulate, simple with about 5 palmatisect primary lobes and pinnatisect secondary lobes, pubescent on both sides like Indian cultivar of 'Bourbon'.

Leaf stem ratio: 2.9:1.
Inflorescence: Raceme, axillary, flowering during April–May.
Flower:

*Pedicel.*—Green with bracts green in colour.
*Calyx.*—Green, pubescent, five sepals.
*Corolla.*—Purple with violet dark streaks on the upper lib of flower, five petals.
*Anther.*—Five, stamens, fused at base.
*Style.*—One.
*Stigma.*—Filamentous (branched) five.
*Seed formation.*—Not observed.

Essential oil content in fresh biomass: 0.25 to 0.30%.

2. Additional description of the plant 'Narmada' of *Pelargonium graveolens*

| SI No. | Chracter | Observation (Mean) | Range |
|---|---|---|---|
| 1. | Plant height | 50.4 cm | 49.0–53.0 cm |
| 2. | Plant width (spread) | 60.4 cm | 55.0–72.0 cm |
| 3. | No. of branches per plant | 7.2 | 6–9 |
| 4. | Internodal length | 2.0 cm | 0.5–3.3 cm |
| 5. | Length of petiole | 7.4 cm | 6.2–9.1 cm |
| 6. | Weight of petiole | 0.5 g | 0.4–0.6 g |
| 7. | Weight of leaf lamina | 1.6 g | 40.8–59.2 $cm^2$ |
| 8. | Leaf size (length × (width) | 47.6 $cm^2$ | 0.65–0.69 $cm^2$ |
| 9. | Leaf shape (length × width) | 0.67 $cm^2$ | 0.65–0.69 $cm^2$ |
| 10. | Leaf form (width × waist | 8.3 $cm^2$ | 7.7–9.4 $cm^2$ |
| 11. | No. of inflorescence/plant | 1 | 0–2 |
| 12. | No. of flower buds/inflorenscence | 4.75 | 4–5 |
| 13. | Herb yield/plant | 423 g | 380–490 g |

The genotype 'Narmada' was developed as a somaclone from the parental cultivar 'Bourbon' and the quality of oil is different from the parental cultivar which in turn different from the existing cultivars. Further RAPD analysis differentiated the plant of invention from the parent and other existing varieties.

In addition to this, we developed the GLC profile of the new plant as mentioned in Table 3, which depicts the chemical profile of the oil of the plant of invention.

TABLE 3

GLC profile of the new plant 'Narmada' of *Pelargonium graveolens*.

| Retention Time (min) | Compound | Area % |
|---|---|---|
| 8.39 | (Z)-3-Hexenol | 0.08 |
| 11.67 | α-pinene | 0.02 |
| 12.98 | Sabinene | 0.04 |
| 13.67 | Myrcene | 0.04 |
| 15.18 | Limonene | 0.05 |
| 15.37 | (Z)-β-ocimene | 0.03 |
| 15.70 | (E)-β-ocimene | 0.07 |
| 16.64 | cis-Linalool oxide | 0.10 |
| 17.17 | Trans-Linalool oxide | 0.04 |
| 17.68 | Linalool | 3.21 |
| 18.05 | cis-Rose oxide | 0.70 |
| 18.65 | Trans-Rose oxide | 0.30 |
| 19.30 | Menthone | 0.28 |
| 19.75 | Isomenthone | 1.32 |

TABLE 3-continued

GLC profile of the new plant 'Narmada' of *Pelargonium graveolens*.

| Retention Time (min) | Compound | Area % |
|---|---|---|
| 20.43 | Terpinen-4-ol | 0.04 |
| 20.85 | α-Terpineol | 0.14 |
| 21.44 | 2,3,-Epoxy-3,7-dimethyl oct-6-en-1-ol | 0.04 |
| 22.31 | Citronellol | 44.28 |
| 23.10 | Geraniol | 16.67 |
| 23.25 | Geranial | 0.96 |
| 23.64 | Citronellyl formate | 8.88 |
| 24.06 | Neryl formate | 0.03 |
| 24.37 | Geranyl formate | 2.99 |
| 25.41 | β-phenylethyl propanoate | 0.09 |
| 25.92 | Citronellyl acetate | 0.30 |
| 26.23 | Neryl acetate | 0.04 |
| 26.44 | α-cubebene | 0.07 |
| 26.71 | Geranyl acetate | 0.40 |
| 27.06 | α-ylangene | 0.07 |
| 27.30 | α-copaene | 0.37 |
| 27.56 | β-bourbonene | 0.43 |
| 28.17 | β-phenyl ethyl buanoate | 0.05 |
| 28.58 | β-caryophyllene | 1.25 |
| 28.81 | Citronellyl propanoate | 0.05 |
| 29.10 | 6,9-guaiadiene | 0.05 |
| 29.39 | Geranyl propanoate | 0.82 |
| 29.52 | α-Humulene | 0.28 |
| 30.04 | γ-Muurolene | 0.07 |
| 30.25 | Germacrene D | 2.29 |
| 30.42 | β-Selinene | 0.03 |
| 30.51 | α-Selinene | 0.13 |
| 30.67 | α-Muurolene | 2.13 |
| 30.98 | Citronellyl butanoate | 0.28 |
| 31.14 | Calamenene | 0.16 |
| 31.23 | δ-cadinene | 0.30 |
| 31.73 | Geranyl butanoate | 0.59 |
| 32.30 | β-Phenylethyl tiglate | 1.08 |
| 32.62 | Furopelargone B | 0.04 |
| 32.78 | Geranyl isovalerate | 0.44 |
| 33.91 | 10-epi-γ-eudesmol | 1.81 |
| 34.12 | Geranyl valerate | 0.04 |
| 34.23 | β-Eudesmol | 0.14 |
| 34.56 | Citronellyl tiglate | 0.11 |
| 35.32 | Geranyl tiglate | 1.99 |
| 36.63 | Geranyl hexanoate | 0.07 |
| 39.09 | Geranyl heptanoate | 0.14 |
| 40.98 | Geranyl octanoate | 0.2 |

The above references are hereby incorporated.

We claim:

1. A new and distinct variety of *Pelargonium graveolens* plant, substantially as shown and described.

* * * * *

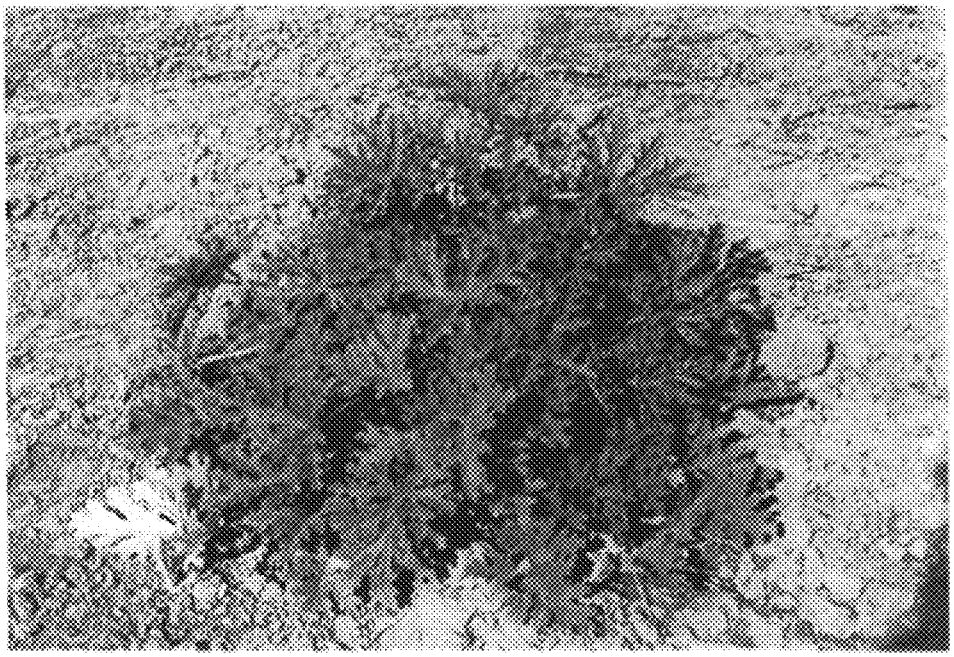
Figure # 1

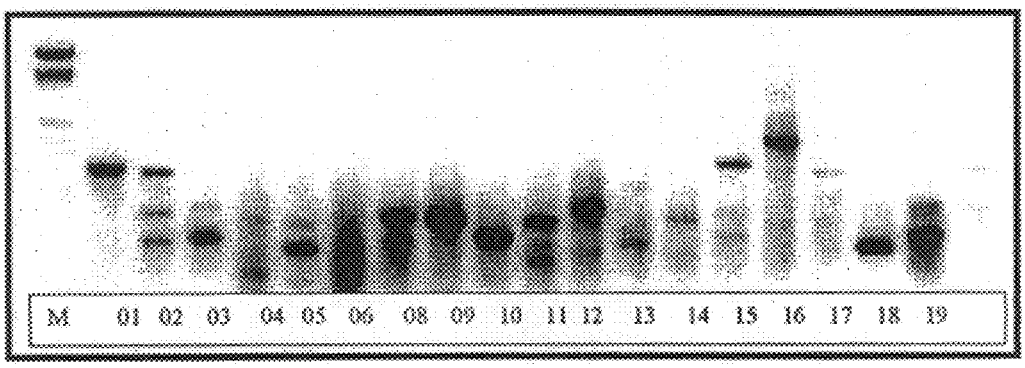
M : λ EcoRI + Hind III digest
Figure # 2 : RAPD profile of Narmada with MAP primers